United States Patent
Pandey et al.

(10) Patent No.: US 9,284,263 B1
(45) Date of Patent: Mar. 15, 2016

(54) PROCESS FOR THE PREPARATION OF(R)-LACOSAMIDE

(71) Applicants: Satyendra Kumar Pandey, Patiala (IN); Yuvraj Garg, Patiala (IN)

(72) Inventors: Satyendra Kumar Pandey, Patiala (IN); Yuvraj Garg, Patiala (IN)

( * ) Notice: Subject to any disclaimer, the term of this patent is extended or adjusted under 35 U.S.C. 154(b) by 0 days.

(21) Appl. No.: 14/656,548

(22) Filed: Mar. 12, 2015

(51) Int. Cl.
*C07C 231/14* (2006.01)

(52) U.S. Cl.
CPC .................... *C07C 231/14* (2013.01)

(58) Field of Classification Search
CPC .................................................. C07C 231/14
See application file for complete search history.

(56) References Cited

FOREIGN PATENT DOCUMENTS

WO    WO 2013/030654    *    3/2013

OTHER PUBLICATIONS

Park, Journal of Medicinal Chemistry, 2009, 52(21), 6897-11.*
LeTiran, Biorganic & Medicinal Chemistry, 2001, 9(10), 2693-2708.*
Trost et al, Angewdt Chemie, 42(48), 5987-5990, 2003.*
Raghunath et al, Tetrahedron Lett, 2005, 46(47), 8213.*

* cited by examiner

*Primary Examiner* — Shailendra Kumar

(57) ABSTRACT

The present invention is directed towards an improved, five step method for the preparation of the anti-epileptic drug (R)-Lacosamide, as illustrated in FIG. 2. The active form of the drug is (R)-enantiomer and the present method gives high yields of (R)-enantiomer of lacosamide. The method does not involve use of any unnatural amino acids as starting material or use of protection/deprotection strategies, strong acids or hydrogenation. Instead, the method uses a cheap and easily available racemic butadiene monoepoxide as the starting material.

16 Claims, 2 Drawing Sheets

FAAs

A (R)-Lacosamide

B

PROCESS FOR THE PREPARATION OF (R)-LACOSAMIDE

FIELD OF INVENTION

The present invention relates to the field of chemical synthesis. More specifically the present invention is directed towards an improved process for the synthesis of the antiepileptic drug (R)-lacosamide.

BACKGROUND OF THE INVENTION

Epilepsy is a common chronic neurological disorder characterized by recurrent unprovoked seizures. These seizures are transient signs and symptoms of abnormal, excessive or synchronous neuronal activity in the brain. Epilepsy thus refers to a clinical phenomenon rather than a single disease entity, since there are many forms and causes of epilepsy. Various methods are available for treating epilepsy including drugs.

The present invention is restricted to anti-epileptic drugs and more specifically to an improved process for the synthesis of the popular anti-epileptic drug viz. (R)-Lacosamide, developed from functionalized amino acids. Functionalized amino acids (FAAs) are an advanced novel class of anticonvulsant agents, from which (R)-Lacosamide emerged as one of the best antiepileptic drugs for the treatment of partial-onset seizures in patients with epilepsy and as add-on treatment in brain tumor patients.

The Structure of FAAs and Lacosamide is Given in FIG. 1 (A and B).

The precise mechanism of action of (R)-Lacosamide in humans has not yet been fully elucidated, but it enhances the slow inactivation of voltage-gated sodium channels, resulting in stabilization of hyperexcitable neuronal membranes and inhibition of repetitive neuronal firing. Additionally, (R)-Lacosamide is also under clinical trials for the treatment of neuropathic pains.

Prior Art Methods of Synthesis of (R)-Lacosamide

Several methods and Schemes have been developed and disclosed in prior art, for the preparation of lacosamide. In general, most of the prior art approaches employed chiral pool approach and start from unnatural amino acid D-serine and its derivatives which are expensive. Methylation is carried out using Kuhn O-methylation which occurs in the presence of expensive catalyst viz. $Ag_2O$ and is commercially not viable due to its high cost, non-regenerability of catalyst and longer reaction time (3-5 days) (Ref: Kuhn, R. *Angew. Chem., Int. Ed. Engl.* 1962, 1, 19).

Very recently, Sebastian Stecko reported the total synthesis of employed Lacosamidestereospecific allylcyanate-to-isocyanate rearrangement, which proceeds with chirality transfer starting from ethyl L-lactate (Ref: Stecko, S. *J. Org. Chem.* 2014, 79, 6342-6346.). However, this approach too suffers from the limitations of long reaction times and cumbersome steps. Limitations of the prior art have been overcome in the process of the present invention which discloses a new, general and highly efficient synthetic approach for the preparation of (R)-Lacosamide. The innovative process of the present invention for the synthesis of (R)-Lacosamide is described in description to the drawings and also illustrated in FIG. 1. The method is overall simple, flexible and highly efficient. The overall yield for (R)-Lacosamide by method of present invention as illustrated in FIG. 1, is about 52% in five steps (a, b, c, d and e). The method of present invention offers the following significant technical advantages:

i. high enantio-selectivity
 ii. high yielding reaction steps
 iii. protection free synthesis
 iv. catalyst regenerability and
 v. cost-effective strategy A comparison of prior art methods with the method of the present invention is given in Table 1 below:

TABLE 1

| Comparison of prior art methods with present invention | | | |
|---|---|---|---|
| Ser. No. | patent application No. | Summary of prior art invention | Comparison with present invention |
| 1. | WO 2011130615 A3 | This synthesis employs chiral pool approach and starting material is unnatural and expensive amino acid 'D-serine' | Method of present invention employs asymmetric synthesis. Starting material is cheap which is easily available racemic material-butadiene monoepoxide. |
| 2. | WO 2011158194 | This synthesis employs enzymatic resolution of racemic Lacosamide, which leads to 50% loss of material. | No enzymatic resolution needed or involved. Direct synthesis of (R)-Lacosamide takes place. No loss of material occurs. |
| 3. | US 20130030216 | Method uses D, L-Serine and proceeds further with diastereomeric resolution of the mixture to precipitate the (R)-enantiomer. Overall this synthesis occurs in seven steps. | No diastereomeric resolution of the mixture or precipitation of the (R)-enantiomer involved at all. Overall synthesis occurs in just five steps, starting from racemic butadiene monoepoxide. |
| 4. | US 20130317109 | Method employs enzymatic acetylation and resolution. | No enzymatic acetylation and resolution involved. Direct enantioselective synthesis of (R)-Lacosamide takes place. |
| 5. | US 20130190533 | Method involves use of catalytic asymmetric hydrogenation, which requires hydrogen gas at high pressure and poses | No hydrogenation involved at all. Process is thus safe and cost effective. |

TABLE 1-continued

Comparison of prior art methods with present invention

| Ser. No. | patent application No. | Summary of prior art invention | Comparison with present invention |
|---|---|---|---|
| | | safety challenges besides increasing cost of process. | |
| 6. | WO 2013072936 A2 | Method involves protection and deprotection of amine moiety, which enhances cost of synthesis. | Method does not involve protection and deprotection of amine moiety or any other group. Therefore, it is cost-effective. |
| 7. | WO 2011144983 | Method employs N-protected D-serine chiral material and N-deprotection, which enhances cost of synthesis. | Method does not employ any kind of protection and deprotection of amine moiety or any other group. Instead it uses asymmetric synthesis starting from the racemic material butadiene monoepoxide. |
| 8. | WO 2011095995 | Method employs chiral pool approach and starts from D-serine followed by Boc protection of the amine moiety and deprotection of Boc group using strong acid. | Method does not use D-Serine as the starting material and neither employs any kind of protection and deprotection of amine moiety or any other functional group. Rather method uses asymmetric synthesis, starting from racemic material butadiene monoepoxide. |
| 9. | WO 2011039781 A1 | Method uses chiral pool approach, starting from D-serine followed by protection/deprotection of the amine moiety and hydroxyl group. | Method neither use D-Serine as the starting material nor employs any kind of protection and deprotection of amine moiety or any other functional group. Rather method uses asymmetric synthesis, starting from racemic material butadiene monoepoxide. |
| 10. | WO 2013072936 A2 | Method employs chiral pool approach and Started from D-serine followed by Boc protection of the amine moiety and deprotection of Boc group using strong acid. | Method neitheremploys chiral pool approach nor does it use D-Serine as the starting material. Further, it does not employ any kind of protection and deprotection of amine moiety or any other functional group. Rather method uses asymmetric synthesis, starting from racemic material butadiene monoepoxide. |
| 11. | WO 2013072330 A1 | Method uses protection/deprotection of the amine moiety followed by dia-stereoselective separation for the pure (R)-Lacosamide, in multisteps. | No protection/ de-protection of the amine moiety involved. No need for dia-stereoselective separation for the pure (R)-Lacosamide. Overall synthesis occurs in just five steps with excellent yield. |
| 12. | WO 2013030654 A1 | Method uses chiral pool approach and starting from D-serine followed by benzyl protection of the amine moiety and hydrogenolysis of benzyl group using hydrogen gas at high pressure. | The present invention employs asymmetric synthesis. Further, it does not employ any kind of protection and deprotection of amine moiety or any other functional group. No hydrogenation is involved at all. Process is thus safe and cost effective. |
| 13. | WO 2014155264 A1 | This invention employs chiral pool approach and uses D-serine as starting material followed by protection/deprotection of the amine moiety. methodinvolves seven steps. | Chiral pool approach is not involved. Rather method uses asymmetric synthesis, starting from racemic material butadiene monoepoxide. Method involves The just 5 steps instead of seven. |
| 14. | US 20140012044 A1 | Method uses expensive and chiral starting material benzyl glycidyl ether and involves Boc protection/ deprotection of the amine moiety using strong acid. Also, method involves hydrogenation which requires hydrogen gas at high pressure. | Our invention does not employ any kind of protection and deprotection of amine moiety or any other group. Our invention also does not employ any hydrogenation process at high pressure so is cost effective and safe for the industrial production. |

DESCRIPTION OF THE DRAWINGS

| FIG. 1 | A: Structure of functionalized amino acids (FAAs) B : Structure of (R)-Lacosamide |
|---|---|
| FIG. 2 | Describes synthesis of (R)-Lacosamide from racemic butadiene monoepoxide by means of Dynamic Kinetic Asymmetric Transformation (DYKAT). The reagents used and the conditions of the reaction for each step, are as below: |
| Step a: | Phthalimide, $Na_2CO_3$, 1.2 mol % (R,R)-DACH, 0.4 mol % $[\eta^3\text{-}C_3H_5PdCl]_2$, dry $CH_2Cl_2$, Room Temperature, 14 hours, about 98% yield |
| Step b: | MeI, NaH, DMF, 0° C. to Room Temperature, 3 hours, about 86% yield |
| Step c: | Two step reaction in one pot (i) $OsO_4$, $NaIO_4$, 2,6-lutidine, dioxane:water (3:1), 0° C. to Room Temperature, 3 hours. (ii) Oxone, DMF, Room Temperature, 3 hours. About 78% yield over two steps. |
| Step d: | $C_6H_5CH_2NH_2$, NMM, IBCF, THF, −78° C. to Room Temperature, 1 hour, about 88% yield |
| Step e: | Two step reaction in one pot (i) $NH_2NH_2 \cdot H_2O$, isopropyl alcohol, 0° C. to Room Temperature, 2 hours. (ii) $CH_3COCl$, $Na_2CO_3$, dry toluene, 0 to 5° C., 1 hour. About 91% yield over two steps. |

OBJECTS OF THE PRESENT INVENTION

The primary object of the present invention is to disclose a simple and cost-effective method for the asymmetric synthesis of the anti-epileptic drug (R)-lacosamide from racemic butadiene monoepoxide as starting material.

Another object of the present invention is to disclose a method for the asymmetric synthesis of antiepileptic drug (R)-lacosamide which has high enantio-selectivity with high yielding reaction steps and catalyst regenerability.

One more object of the invention is to disclose an improved method for the synthesis of Lacosamide which does not involve use of any protection/de-protection strategies, strong acids or hydrogenation, so is cost-effective.

Abbreviations
i. (R,R)-DACH: (1R,2R)-(+)-1,2-Diaminocyclohexane-N, N'-bis(2 dinaphthylphosphinobenzoyl)
ii. DYKAT: Dynamic Kinetic Asymmetric Transformation
iii. THF: Tetrahydrofuran
iv. $OsO_4$: Osmium tetroxide
v. DMF: Dimethylformamide
vi. $NaIO_4$: Sodium periodate
vii. NMM: N-Methylmorpholine
viii. IBCF: Isobutylchloroformate
ix. (R)—R isomer or R enantiomer
x. (S)—S isomer or S enantiomer

SUMMARY OF THE PRESENT INVENTION

The present invention is directed towards an improved method for the preparation of the anti-epileptic drug lacosamide (FIG. 1B). The active form of the drug is (R)-enantiomer and the present method gives high yields of (R)-enantiomer of lacosamide. Unlike prior art methods, the improved method of present invention does not involve use of any protection/deprotection strategies, strong acids or hydrogenation. The synthetic route involved in the improved method is given in FIG. 2.

DETAILED DESCRIPTION OF THE INVENTION

Figure 2:
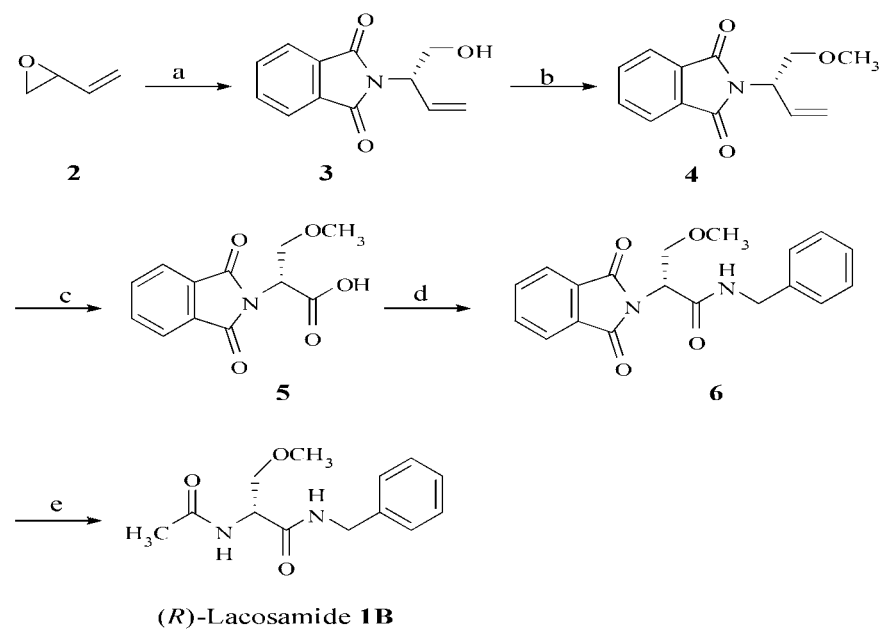

The synthesis of (R)-Lacosamide is started from commercially available racemic butadiene monoepoxide and is described in FIG. 2, Steps a to e.

Butadiene monoepoxide can be easily synthesized using silver-catalyzed oxidation of 1,3-butadiene (Ref: Monnier, J. R.; Muehlbauer, P. J. Patent US 508096, Published 1992; Chem. Abstr. 1992, 116, 11439; U.S. Pat. No. 5,138,077, 1992)

The five steps, Step a to Step e, involved in the synthesis of (R)-Lacosamide by the process of the present invention, are as given below:

Step a: De-Racemisation

Deracemisation of butadiene monoepoxide (FIG. 2, No. 2) with palladium catalyzed Trost's Dynamic Kinetic Asymmetric Transformation (DYKAT) in the presence of chiral ligand 1.2 mol % (R,R)-DACH and 0.4 mol % $[\eta^3\text{-}C_3H_5PdCl]_2$, phthalimide and base $Na_2CO_3$ afforded asymmetric allylic alkylation (AAA) product phthaloyl alcohol (FIG. 2, No. 3) as a single enantiomer with about 98% yield with ≥99% ee $\{[\alpha]_D^{25}$ −72.2 (c 2.02, $CH_2Cl_2$) [Lit. −72.2 (c 2.02, $CH_2Cl_2$) (Ref: Trost, B. M.; Bunt, R. C.; Lemoine, R. C.; Calkins, T. L. J. Am. Chem. Soc. 2000, 122, 5968-5976).

Conditions and Yield:
Phthalimide, $Na_2CO_3$, 1.2 mol % (R,R)-DACH, 0.4 mol % $[\eta^3\text{-}C_3H_5PdCl]_2$, dry $CH_2Cl_2$, Room Temperature, 14 hours, about 98% yield.

Step b: Methylation

The enantiomerically pure alcohol (FIG. 2, No. 3) was then subjected to O-methylation with MeI in presence of NaH which afforded methyl ether (FIG. 2, No. 4) in 86% yield.

Conditions and Yield:
MeI, NaH, DMF, 0° C. to Room Temperature, 3 hours, about 86% yield.

Step c: Oxidative Cleavage and Acid Formation:

The next step was to carry out amide formation at terminal double bond site. For this, the compound methyl ether (FIG. 2, No. 4) was subjected to oxidative cleavage in the presence of $OsO_4$ and sodium periodate followed by oxidation with oxone at room temperature, which led to formation of phthaloyl acid (FIG. 2, No. 5).

Conditions and Yield:
The reaction is carried out as two step reaction in one pot:
(i) $OsO_4$, $NaIO_4$, 2,6-lutidine, dioxane:water (3:1), 0° C. to Room Temperature, 3 hours
(ii) Oxone, DMF, Room Temperature, 3 hours (about 78% yield over two steps).

Step d: Amide Formation:

The treatment of phthaloyl acid (FIG. 2, No. 5) with benzyl amine in presence of isobutylchloroformate and N-methyl morpholine in THF at −78° C. afforded the phthaloyl amide (FIG. 2, No. 6) in about 88% yield.

Conditions and Yield:
$C_6H_5CH_2NH_2$, NMM, IBCF, THF, −78° C. to Room Temperature, 1 hour, about 88% yield.

Step e: Phthalimide Cleavage and Acetylation:

Finally, the cleavage of phthalimide group of phthaloyl amide (R) (FIG. 2, No. 6) with hydrazine hydrate in presence of isopropyl alcohol followed by N-acetylation using acetyl chloride under basic conditions furnished the target compound (R)-Lacosamide (FIG. 1B) in about 91% yield $\{[\alpha]_D^{25}$ +16.1 (c 1, MeOH) [Lit. +16.2 (c 1, MeOH),[5g] +16.1 (c 1.2, MeOH)[5h]]$\}$. The spectroscopic and physical data of (R)-Lacosamide (FIG. 1B) were in full agreement with literature data.

Conditions and Yield:
The reaction is carried out as a two step reaction in one pot:
(i) $NH_2NH_2 \cdot H_2O$, isopropyl alcohol, 0° C. to Room Temperature, 2 hours
(ii) $CH_3COCl$, $Na_2CO_3$, dry toluene, 0 to 5° C., 1 hour. About 91% yield over two steps

Illustration of Technical Aspects

In the following section, technical aspects are described by way of examples to illustrate the process of the invention. However, these do not limit the scope of the present invention. Several variants of these examples would be evident to persons ordinarily skilled in the art.

All reactions were carried out under argon or nitrogen in oven-dried glassware using standard glass syringes, cannulas and septa. The solvents were dried and purified by standard procedures prior to use. Infrared spectra (IR) were run on Agilent resolution Pro 600. Optical rotations were obtained on automatic polarimeter AA-65. $^1$H NMR and $^{13}$C NMR spectra were obtained at 400 MHz and 100 MHz respectively on JEOL ECS-400 MHz spectrometer using TMS as internal reference standard. The reactions were monitored on TLC plates Merck silica gel 60 F254 and visualization with UV light, ninhydrin, anisaldehyde in ethanol and 2,4-Dinitrophenylhydrazine as developing reagents. High resolution Mass spectra (HRMS) were recorded on Agilent 6530 accurate-mass Q-TOF using electron spray ionization.

EXAMPLE 1

Preparation of (S)-2-(Isoindolin-2-yl)but-3-en-1-ol (FIG. 2, No. 3)

A mixture of π-allylpalladium chloride dimer 0.4 mol % (20 mg, 53 μmol), 1.2 mol % (R,R)-DACH ligand (125 mg, 158 μmol, $Na_2CO_3$ (70 mg, 0.66 mmol) and phthalimide (1.94 g, 13.2 mmol) in 100 mL of dry $CH_2Cl_2$ was purged with nitrogen for 1 h. The resulting mixture was stirred for 10 min at room temperature to which butadiene monoepoxide (FIG. 2, No. 2) (920 mg, 13.2 mmol) was added. The resulting mixture was stirred at room temperature under nitrogen for 14 h, concentrated in vacuo and purified by silica gel column chromatography using ethyl acetate/hexane (3:7) as eluent furnished 2.8 g (98%) yield of (S)-2-(Isoindolin-2-yl) but-3-en-1-ol (FIG. 2, No. 3) as a crystalline white solid. [$R_f$=0.21, ethyl acetate/hexane (3:7)]; $[\alpha]_D^{25}$ −72.2 (c 2.02, $CH_2Cl_2$) [Lit. −72.2 (c 2.02, $CH_2Cl_2$)]; IR ($CH_2Cl_2$) v: 3467, 1773, 1698, 1467, 1383 cm$^{-1}$; $^1$H NMR (400 MHz, CDCl$_3$) δ: 2.7 (bs, 1H), 3.9 (m, 1H), 4.1 (m, 1H), 4.9 (m, 1H), 5.2 (m, 2H), 6.1 (ddd, J=6.4 Hz, 1H), 7.7 (dd, J=3.2, 5.48 Hz, 2H), 7.8 (dd, J=2.76, 5.48 Hz, 2H); $^{13}$C NMR (100 MHz, CDCl$_3$) δ: 55.9, 62.8, 118.8, 123.4, 131.7, 131.9, 134.2, 168.5. (Ref: Trost, B. M et al. *J. Am. Chem. Soc.* 2000, 122, 5968-597).

EXAMPLE 2

Preparation of (S)-2-(1-Methoxybut-3-en-2-yl)isoindoline (FIG. 2, No. 4)

To a solution of (S)-2-(Isoindolin-2-yl) but-3-en-1-ol (FIG. 2, No. 3)(2.0 g, 9.2 mmol) in 40 mL DMF was successively added NaH (442 mg, 18.4 mmol) at 0° C., stirred for ten minutes followed by addition of MeI (1.73 mL, 27.6 mmol) and then the reaction mixture was stirred at room temperature for 3 h. The reaction mixture was quenched by addition of ice cold water, extracted with diethyl ether, washed with brine and dried over anhydrous $MgSO_4$. The organic layer was then concentrated in vacuo and purified by silica gel column chromatography using ethyl acetate/hexane (1:9) as eluent to furnish 1.83 g (86%) yield of (S)-2-(1-Methoxybut-3-en-2-yl) isoindoline (FIG. 2, No. 4) as a crystalline white solid. [$R_f$=0.56, ethyl acetate/hexane (3:7)]; $[\alpha]_D^{25}$ −75.1 (c 1.0, $CH_2Cl_2$); IR ($CH_2Cl_2$) v: 1773, 1708, 1468, and 1384 cm$^{-1}$; $^1$H NMR (400 MHz, CDCl$_3$) δ:3.3 (s, 3H), 3.6 (m, 1H), 4.06 (m, 1H), 5.0 (m, 1H), 5.22-5.31 (m, 2H), 6.12 (ddd, J=7.32 Hz, 1H), 7.68 (dd, J=2.76, 5.48 Hz, 2H), 7.80 (dd, J=2.76, 5.48 Hz, 2H); $^{13}$C NMR (100 MHz, CDCl$_3$) δ: 52.8, 58.7, 71.3, 119.0, 123.2, 131.9, 132.1, 133.9, 168.0; HRMS (ESI-TOF) m/z calcd for $C_{13}H_{13}NO_3Na$ [M+Na$^+$] 254.080. Found 254.079.

EXAMPLE 3

Preparation of (R)-2-(Isoindolin-2-yl)-3-methoxypropanoic acid (FIG. 2, No. 5)

To a solution of compound (S)-2-(1-Methoxybut-3-en-2-yl) isoindoline (FIG. 2, No. 4)(1.5 g, 6.5 mmol) indioxane-water (3:1, 40 mL) was added 2,6-lutidine (1.5 mL, 13 mmol), $OsO_4$ (0.1 M solution in toluene, 1.3 mL, 0.13 mmol) and $NaIO_4$ (2.78 g, 13 mmol). The reaction was stirred at 25° C. for 3 h. After completion of reaction, water (10 mL) and $CH_2Cl_2$ (30 mL) were added. The organic layer was separated, and the water layer extracted with $CH_2Cl_2$ (3×10 mL). The combined organic layer was washed with brine and dried over anhydrous $MgSO_4$, concentrated in vacuo to give crude aldehyde which was used as such for the next step without further purification.

The above aldehyde was dissolved in DMF and oxone (2 g, 6.5 mmol) was added in one portion and stirred at room temperature for 3 h. The resulting solution was diluted with water, filtered through a celite pad, washed and extracted with diethyl ether (3×20 mL). The organic extract was washed with brine, dried over anhydrous $MgSO_4$, and the solvent was removed in vacuo to obtain the crude product (R)-2-(Isoindolin-2-yl)-3-methoxypropanoic acid (FIG. 2, No. 5) (1.26 g, 78%, yield determined by $^1$H NMR) which was used as such for the next step without further purification due to its more polar nature. The analytical sample was obtained by preparative chromatography on silica gel ($CH_2Cl_2$:MeOH, 9:1) as yellow oil. $[\alpha]_D^{25}$ +66.5 (c 0.1, MeOH); IR ($CH_2Cl_2$) v: 2896, 1775, 1699, 1604 and 1392 cm$^{-1}$; $^1$H NMR (400 MHz, CDCl$_3$) δ:3.36 (s, 3H), 4.0 (m, 1H), 4.17 (t, J=10.08 Hz, 1H), 5.17-5.20 (m, 1H), 7.74 (dd, J=3.2, 5.52 Hz, 2H), 7.86 (dd, J=3.2, 5.52 Hz, 2H), 8.05 (bs, 1H); $^{13}$C NMR (100 MHz, CDCl$_3$) δ: 56.0, 62.9, 118.9, 123.5, 131.8, 132.0, 134.2, 168.6; HRMS (ESI-TOF) m/z calcd for $C_{12}H_{11}NO_5Na$ [M+Na$^+$] 272.050. Found 272.05.

EXAMPLE 4

Preparation of (R)—N—Benzyl-2-(isoindolin-2-yl)-3-methoxypropanamide (FIG. 2, No. 6)

To the crude acid (R)-2-(Isoindolin-2-yl)-3-methoxypropanoic acid (FIG. 2, No. 5)(1.25 g, 5 mmol) in dry THF was added N-methylmorpholine (0.66 mL, 6.0 mmol) at −78° C. under an argon atmosphere. After 5 min, isobutyl chloroformate (0.78 mL, 6.0 mmol) was added and stirred for another 5 min. To this reaction mixture benzylamine (0.65 mL, 6.0 mmol) was added at −78° C. after which the reaction mixture was stirred at room temperature for 1 h. After completion of the reaction, the reaction mixture was filtered through a celite pad, washed with ethyl acetate, and dried over anhydrous $MgSO_4$. The solvent was removed in vacuo and the crude product was subjected to silica gel column chromatography (Ethyl acetate/Hexane, 4:6) to yield 1.48 g, 88% yield of (R)—N—Benzyl-2-(isoindolin-2-yl)-3-methoxypropanamide (FIG. 2, No. 6) as a crystalline solid. [$R_f$=0.26, ethyl acetate/hexane (4:6)]; $[\alpha]_D^{25}$ +81.8 (c 1, $CH_2Cl_2$); IR (CH$_2$Cl$_2$) v: 1718, 1685, 1535, and 1387 cm$^{-1}$; $^1$H NMR (400 MHz, CDCl$_3$) δ:3.38 (bs, 3H), 3.75 (m, 1H), 4.34 (t, J=9.64 Hz, 1H), 4.46 (m, 2H), 5.0 (m, 1H), 7.1 (bs, 1H), 7.21-7.33 (m, 5H), 7.7 (dd, J=3.2, 5.48 Hz, 2H), 7.83 (dd, J=3.2, 5.48 Hz, 2H); $^{13}$C NMR (100 MHz, CDCl$_3$) δ: 29.6, 43.5, 51.7, 58.9, 70.1, 123.5, 127.1, 127.3, 127.4, 128.4, 128.6, 131.8, 134.1, 137.9, 167.3, 167.9; HRMS (ESI-TOF) m/z calcd for C$_{19}$H$_{18}$N$_2$O$_4$Na [M+Na$^+$] 361.120. Found 361.116.

EXAMPLE 5

Figure 1:
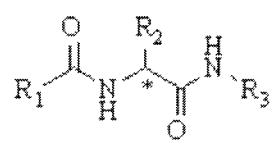
Figure 1:
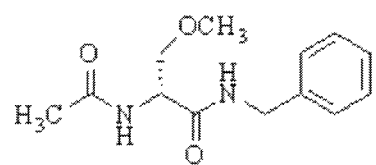

Preparation of the Final Product (R)-Lacosamide
(FIG. 1, No. B)

To a solution of the compound (R)—N—Benzyl-2-(isoindolin-2-yl)-3-methoxypropanamide (FIG. 2, No. 6) (1.4 g, 4.1 mmol) in 20 mL of isopropyl alcohol was added hydrazine monohydrate (0.22 mL, 4.5 mmol) at 0° C. under nitrogen atmosphere. The reaction was stirred at 25° C. for 2 h. The resulting solution was filtered, washed with diethyl ether, brine, dried over magnesium sulphate and concentrated in vacuo to furnish the crude compound [R$_f$=0.36, CH$_2$Cl$_2$:MeOH (9:1)]. The resulting crude was used as such for the next step without further purification.

The residue was then dissolved in dry toluene followed by addition of Na$_2$CO$_3$ (1.3 g, 12.3 mmol) was added. The reaction mixture was cooled to 0° C. after which acetyl chloride (0.33 mL, 4.5 mmol) was slowly added and the solution stirred at 5° C. for 1 h. After completion of the reaction, the solid was filtered through a celite pad and the solvent was evaporated in vacuo. The crude product was purified by silica gel column chromatography (CH$_2$Cl$_2$:MeOH, 95:05) to afford 935 mg (91%) yield of (R)-Lacosamide (FIG. 1, No. B) as white solid [R$_f$=0.47, CH$_2$Cl$_2$:MeOH (9:1)]; mp 143-144° C. [Lit. 140-141° C., 142-143° C.]; [α]$_D^{25}$ +16.1 (c 1, MeOH) [Lit. +16.2 (c 1, MeOH), +16.1 (c 1.2, MeOH),]; IR (CH$_2$Cl$_2$) v: 3054, 2928, 1650, 1529, 1372, 1264, and 1118 cm$^{-1}$; $^1$H NMR (400 MHz, CDCl$_3$) δ:2.02 (s, 3H), 3.37 (s, 3H), 3.44 (m, 1H), 3.80 (m, 1H), 4.47 (m, 2H), 4.57 (m, 1H), 6.54 (s, 1H), 6.86 (s, 1H), 7.24-7.68 (m, 5H); $^{13}$C NMR (100 MHz, CDCl$_3$) δ: 23.2, 43.5, 52.3, 59.0, 71.6, 127.4, 127.4, 128.7, 137.8, 169.9, 170.3.
(Ref: Wadavrao et al. *Synthesis* 2013, 45, 3383-3386; Stecko, S. *J. Org. Chem.* 2014, 79, 6342-6346).

Novelty

The present invention discloses a new process for the synthesis of the anti-epileptic drug (R)-Lacosamide, which has not been disclosed in the prior art. Unlike prior art methods which use expensive starting materials e.g. unnatural amino acids such as D-Serine, the present method (FIG. 2, Steps a to e) uses a cheap and easily available racemic material-butadiene monoepoxide. Also, the process is completed in just five steps, does not involve use of any protection/deprotection strategies or use of any strong acid or hydrogenation.

Inventive Step

The technical advancement of knowledge, as disclosed in the present invention lies in synthesizing the active form of the anti-epileptic drug, (R)-Lacosamide using a new route as disclosed in FIG. 1, Steps a to e.

INDUSTRIAL APPLICATION

The drug (R)-Lacosamide is widely used for the treatment of epilepsy. The present invention discloses an easy, cost-effective process for its synthesis and thus has widespread industrial application.

We claim:
1. A process for synthesis of >99% ee enantio-pure (R)-Lacosamide from racemic butadiene monoepoxide and the said process comprising the five steps of:

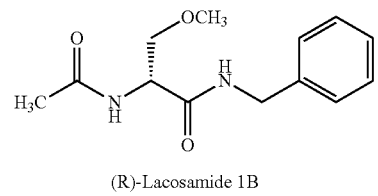 [SMILES: COC[C@@H](NC(C)=O)C(=O)NCc1ccccc1]

(R)-Lacosamide 1B i. Deracemisation: of butadiene monoepoxide 2 with palladium catalyzed Trost's DYKAT in the presence of chiral ligand 1.2 mol % (R,R)-DACH and 0.4 mol % [η$^3$-C$_3$H$_5$PdCl]$_2$, phthalimide and base Na$_2$CO$_3$ at room temperature for period of 14 hours afforded asymmetric allylic alkylation (AAA) product phthaloyl alcohol

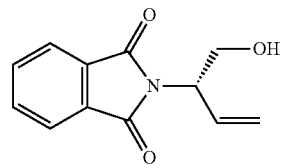

3 ii. Methylation: preparing methyl ether (S)-4 from phthaloyl alcohol (S)-3 with methyl iodide under basic conditions in solvent at temperature in the range of 0° C. to Room Temperature for period of 3 hours;

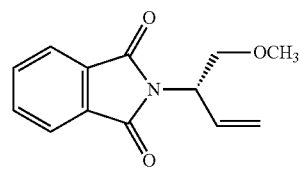

4 iii. Oxidative cleavage and acid formation: oxidative cleavage of the terminal double bond of (S)-4 in the presence of osmium tetraoxide and sodium periodate in solvent at temperature in the range of 0° C. to Room Temperature for period of 3 hours followed by oxidation with oxone in solvent at room temperature for period of 3 hours afforded (R)-5;

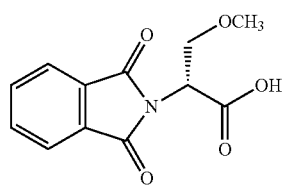

5 iv. Amide formation: amide formation of (R)-5 as obtained in step (iii) with benzyl amine in the presence of isobutylchloroformate and N-methylmorpholine in solvent at temperature in the range of −78° C. to Room Temperature for period of 1 hour 1 hour afforded (R)-6;

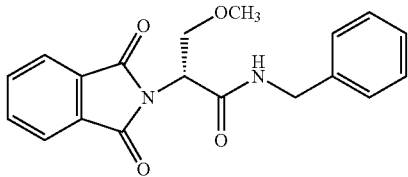

v. Phthalimide cleavage and acetylation: cleavage of phthalimide group of amide (R)-6 as obtained in step (iv) with hydrazine hydrate in solvent followed by N-acetylation in the presence of acetylating agent, base and solvent to obtain (R)-Lacosamide 1B.

2. The process as claimed in step (i) of claim 1, wherein the base is a metal carbonate.

3. The process as claimed in step (i) of claim 1, wherein the epoxide is allylic epoxide.

4. The process as claimed in step (ii) of claim 1, wherein the base is selected from the group consisting of metal hydrides, hydroxides, oxides, carbonates, bicarbonates, alkoxides or primary and secondary amine, ammonia, alkyl amine.

5. The process as claimed in step (iii) of claim 1, wherein the oxidizing agent is selected from the group consisting of PDC, PCC, $KMnO_4$, Oxone, $NaClO_2$.

6. The process as claimed in step (iv) of claim 1, wherein temperature is in the range of −100° C. to Room Temperature.

7. The process as claimed in step (v) of claim 1, wherein the acetylating agent used is selected from the group consisting of acetic anhydride, acetyl chloride, acetic acid and mixture thereof or suitable derivatives thereof.

8. The process as claimed in step (v) of claim 1, wherein the base is selected from the group consisting of carbonates, bicarbonates, hydroxides, hydrides, alkoxides, aryl amines, aliphatic amines, heterocyclic compound and like thereof.

9. The process as claimed in step (v) of claim 1, wherein solvent used is selected from group consisting of esters, ketones, aliphatic or aromatic hydrocarbons, acids, nitriles, water, aldehydes, alcohols, halides, non-polar solvents and mixture thereof.

10. The process as claimed in claim 9, wherein solvent used is selected from the group consisting of toluene, methanol, ethanol, acetonitrile, THF, acetone, petroleum ether, n-hexane, isopropanol, acetic acid, ethyl acetate, dichloromethane, water, water miscible solvents or mixtures thereof.

11. The process as claimed in claim 1, wherein yield of the said (R)-Lacosamide is 52%.

12. The process as claimed in step (i) of claim 1, wherein the base is selected from the group consisting of $Na_2CO_3$, $K_2CO_3$.

13. The process as claimed in step (i) of claim 1, wherein the epoxide is butadiene monoepoxide.

14. The process as claimed in step (ii) of claim 1, wherein the base is a metal hydride.

15. The process as claimed in step (iii) of claim 1, wherein the oxidizing agent is oxone.

16. The process as claimed in step (iv) of claim 1, wherein temperature is in the range of −78° C. to Room Temperature.

* * * * *

UNITED STATES PATENT AND TRADEMARK OFFICE
CERTIFICATE OF CORRECTION

| | | |
|---|---|---|
| PATENT NO. | : 9,284,263 B1 | Page 1 of 1 |
| APPLICATION NO. | : 14/656548 | |
| DATED | : March 15, 2016 | |
| INVENTOR(S) | : Satyendra Kumar Pandey et al. | |

It is certified that error appears in the above-identified patent and that said Letters Patent is hereby corrected as shown below:

Title Page, Foreign Application Priority Data: Please insert
--INDIA, 324/DEL/2015, 2/4/2015--

Signed and Sealed this
Fifth Day of July, 2016

Michelle K. Lee
*Director of the United States Patent and Trademark Office*